(12) United States Patent
Guirguis (10) Patent No.: US 7,741,103 B2
(45) Date of Patent: Jun. 22, 2010

(54) INTEGRATED SCREENING AND CONFIRMATION DEVICE

(76) Inventor: Raouf A. Guirguis, 1712 Brookside La., Vienna, VA (US) 22182

( * ) Notice: Subject to any disclaimer, the term of this patent is extended or adjusted under 35 U.S.C. 154(b) by 0 days.

(21) Appl. No.: 11/394,189

(22) Filed: Mar. 31, 2006

(65) Prior Publication Data
US 2007/0239069 A1  Oct. 11, 2007

(51) Int. Cl.
G01N 33/543 (2006.01)
G01N 33/558 (2006.01)

(52) U.S. Cl. ............... 435/287.1; 422/56; 422/57; 422/58; 435/287.2; 435/287.7; 435/287.9; 435/810; 435/970; 436/514; 436/807; 436/810

(58) Field of Classification Search .............. None
See application file for complete search history.

(56) References Cited

U.S. PATENT DOCUMENTS

| | | |
|---|---|---|
| 3,784,358 A | 1/1974 | Drake, Jr. |
| 4,632,901 A | 12/1986 | Valkirs et al. |
| 4,717,656 A | 1/1988 | Swanljung |
| 4,774,192 A | 9/1988 | Terminiello et al. |
| 4,775,636 A | 10/1988 | Moeremans et al. |
| 4,810,630 A | 3/1989 | Craig et al. |
| 4,817,632 A | 4/1989 | Schramm |
| 4,826,759 A | 5/1989 | Guire et al. |
| 4,853,335 A | 8/1989 | Olsen et al. |
| 4,883,764 A | 11/1989 | Kloepfer |
| 4,959,324 A | 9/1990 | Ramel et al. |
| 4,963,325 A | 10/1990 | Lennon et al. |
| 5,006,464 A | 4/1991 | Chu et al. |
| 5,028,535 A | 7/1991 | Buechler et al. |
| 5,071,746 A | 12/1991 | Wilk et al. |
| 5,079,029 A | 1/1992 | Saunders et al. |
| 5,079,172 A | 1/1992 | Hari et al. |
| 5,104,619 A | 4/1992 | De Castro et al. |
| 5,221,627 A | 6/1993 | Grigg et al. |
| 5,244,815 A * | 9/1993 | Guirguis ............... 436/530 |
| 5,260,031 A | 11/1993 | Seymour |
| 5,268,148 A | 12/1993 | Seymour |

(Continued)

FOREIGN PATENT DOCUMENTS

EP  0 200 381  11/1986

(Continued)

OTHER PUBLICATIONS

International Search Report for application No. PCT/US07/07956, mailed Apr. 9, 2008.

(Continued)

Primary Examiner—Christopher L Chin
(74) Attorney, Agent, or Firm—Hunton & Williams LLP (57) ABSTRACT

The present invention provides a fluid collection and drug testing device that includes a fluid collector, to collect a fluid sample, and a housing to test and retain the fluid sample. The housing includes a collection chamber, having an open end to receive the fluid collector, at least one membrane test strip, in fluid communication with the collection chamber, to indicate the presence or absence of at least one test drug, and an immunoassay-based fingerprint acquisition pad, in fluid communication with the collection chamber, to positively identify the test subject and associate the test subject with the fluid sample.

22 Claims, 9 Drawing Sheets

Front View

U.S. PATENT DOCUMENTS

| | | | |
|---|---|---|---|
| 5,270,167 | A | 12/1993 | Francouer |
| 5,283,038 | A | 2/1994 | Seymour |
| 5,308,580 | A | 5/1994 | Clark |
| 5,342,645 | A | 8/1994 | Eisele et al. |
| 5,376,337 | A | 12/1994 | Seymour |
| 5,378,492 | A | 1/1995 | Mashiko |
| 5,380,492 | A | 1/1995 | Seymour |
| 5,393,496 | A | 2/1995 | Seymour |
| 5,416,000 | A | 5/1995 | Allen et al. |
| 5,441,698 | A | 8/1995 | Norell |
| 5,468,648 | A | 11/1995 | Chandler |
| 5,494,646 | A | 2/1996 | Seymour |
| 5,629,164 | A | 5/1997 | Rivers |
| 5,869,345 | A | 2/1999 | Chandler |
| 5,876,926 | A | 3/1999 | Beecham |
| 5,935,864 | A | 8/1999 | Schramm et al. |
| 6,352,863 | B1 * | 3/2002 | Guirguis ............ 436/534 |
| 6,365,417 | B1 * | 4/2002 | Fleming et al. ............ 436/514 |
| 6,766,817 | B2 | 7/2004 | Da Silva |
| 7,060,505 | B2 * | 6/2006 | Guirguis ............ 436/514 |
| 2002/0160538 | A1 * | 10/2002 | Guirguis ............ 436/539 |
| 2004/0029261 | A1 | 2/2004 | Oldfield |
| 2004/0235192 | A1 * | 11/2004 | Guirguis ............ 436/518 |
| 2006/0000894 | A1 | 1/2006 | Bonalle et al. |
| 2007/0179436 | A1 | 8/2007 | Braig et al. |
| 2007/0239069 | A1 | 10/2007 | Guirguis |
| 2008/0194041 | A1 | 8/2008 | Guirguis |

FOREIGN PATENT DOCUMENTS

| | | |
|---|---|---|
| EP | 0 203 238 | 12/1986 |
| EP | 0 440 350 A2 * | 8/1991 |
| WO | WO 92/16842 * | 10/1992 |
| WO | WO 93/06486 * | 4/1993 |

OTHER PUBLICATIONS

International Search Report for application No. PCT/US09/00829, mailed Apr. 2, 2009.

Cone et al. Stability of Cocaine In Saliva Clinical Chemistry vol. 34(7) p. 1508 (1988).

Schramm et al. An Ultrafiltrate Of Saliva Collected In Situ As A Biological Sample For Diagnostic Evaluation Clinical Chemistry vol. 37(1) pp. 114-115 (1991).

Wolff et al. Methadone In Saliva Clinical Chemistry vol. 37(7) pp. 1297-1298 (1991).

http://www.craigmedical.com/products.htm visited Jan. 2006.

* cited by examiner

FIG. 1

*Front View*

FIG. 2

*Top View*

FIG. 3

Back View

*Front View*

FIG. 7

*Front View*

FIG. 8

*Back View*

FIG. 9

Back View

INTEGRATED SCREENING AND CONFIRMATION DEVICE

FIELD OF THE INVENTION

The present invention relates to substance testing. More particularly, the present invention relates to a device that tests a fluid sample, collected from a test subject, for the presence or absence of one or more particular substances, positively identifies the test subject and secures the fluid sample for later confirmation.

BACKGROUND OF THE INVENTION

Drug testing has become ubiquitous in modern society. From the workplace, to athletics, to law enforcement, etc., effective, inexpensive and reliable drug testing devices have been sought. The marketplace has responded and is replete with many such devices directed to the testing of blood, urine or saliva. However, these devices may require a series of tests involving the shifting of the fluid sample being tested to different containers and/or the removal of the fluid sample to distant locations. One simple test device includes a single card containing several membrane test strips, the exposed ends of which are dipped into a fluid sample. One company, Craig Medical Distribution, Inc., advertises several urine and saliva-based drug test devices (See, http://www.craigmedical.com/products.htm, visited January 2006).

Oftentimes, the chain of custody associated with these devices imbues the results with doubt, as the fluid sample may become contaminated, misplaced or a different fluid sample may be substituted entirely. For the membrane test strip device described above, the fluid sample may not even be retained. In many instances, identification of the test subject associated with the fluid sample is critically dispositive. Moreover, further confirmation testing of the fluid sample, using more sophisticated tests and analyses, is often required. These goals are practically impossible to achieve using current devices and methods. Thus, a need exists in the industry to combine the simplicity of current membrane test strip technology with the ability to positively identify the test subject, as well as the capability to secure the fluid sample for later confirmation, within a single device.

SUMMARY OF THE INVENTION

Embodiments of the present invention provide a fluid collection and drug testing device that includes a fluid collector, to collect a fluid sample, and a housing to test and retain the fluid sample. The housing includes a collection chamber, having an open end to receive the fluid collector, at least one membrane test strip, in fluid communication with the collection chamber, to indicate the presence or absence of at least one test drug, and an immunoassay-based fingerprint acquisition pad, in fluid communication with the collection chamber, to positively identify the test subject and associate the test subject with the fluid sample.

BRIEF DESCRIPTION OF THE DRAWINGS

The above and other advantages of this invention will become more apparent by the following description of invention and the accompanying drawings.

DETAILED DESCRIPTION

Embodiments of the present invention provide an oral fluid drug screening device which combines a rapid screening, lateral flow chromatographic immunoassay for the simultaneous, qualitative detection of drugs, including, for example, amphetamine, methamphetamine, cocaine, opiates, THC and PCP and their metabolites in human fluid (e.g., oral fluid), with immunoassay-based fingerprint identification of the test subject. Embodiments of the present invention also securely preserve the fluid sample for further confirmation testing.

Lateral flow chromatographic immunoassay tests are based on the principle of competitive binding—drugs that may be present in a fluid sample compete against their respective drug conjugate for binding sites on their specific antibody. In various embodiments of the present invention, monoclonal antibodies are used to selectively detect elevated levels of specific drugs in the test subject fluid. For example, a porous membrane test strip may be coated with drug-protein conjugates in the test region, a control-protein conjugate in the control region and colored antibodies in a dye pad region. In one embodiment, the control-protein conjugate is a goat polyclonal antibody against gold protein conjugate, while the dye pad region contains colloidal gold particles coated with mouse monoclonal antibodies specific to the various drugs to be tested.

After the fluid sample is introduced into the membrane test strip near the dye pad region, a portion of the fluid sample migrates upward by capillary action. If a drug is present in the fluid sample below a predetermined concentration, the drug will not saturate the binding sites of the drug's specific antibody. As the fluid sample migrates upward across the membrane test strip, the antibody is carried upward as well. Once the antibody reaches the test region, the antibody reacts with the drug-protein conjugate and a colored line will become visible in the test region. Conversely, if a drug is present in the fluid sample above the predetermined concentration, the drug will saturate the binding sites of the drug's specific antibody. As the fluid sample migrates upward, the antibody is no longer free to react with the drug-protein conjugate, and no colored line will appear. The reaction of the control-protein conjugate with other colored antibodies produces a colored line in the control region, indicating that a proper volume of the fluid sample has been added and that membrane wicking has occurred.

Thus, a drug-positive fluid specimen will not generate a colored line in the test region of the membrane test strip due to the presence of drug competition, while a drug-negative fluid sample will generate a line in the test region due to the absence of drug competition.

Various embodiments of the immunoassay-based fingerprint identification are contemplated by the present invention. Several embodiments are described within U.S. Pat. No. 6,352,863 to Raouf A. Guirguis, issued Mar. 5, 2002 (the "'863 patent"), and U.S. Pat. No. 5,244,815 to Raouf A. Guirguis, issued Sep. 14, 1993 (the "'815 patent"), which are incorporated herein by reference in their entirety. Other embodiments, described below, may incorporate various features of the embodiments disclosed within the '863 and '815 patents.

FIGS. 1-5 depict a fluid collection and drug testing device in accordance with an embodiment of the present invention. In this embodiment, fingerprint drug screening device 10 includes a fluid collector 20, to collect a fluid sample from a test subject, and a housing 30 to test and retain the fluid sample. The housing 30 contains a collection chamber 40, to receive the fluid collector 20 through an opening 32, one or more membrane test strips 51, to indicate the presence or absence of one or more drugs, and an immunoassay-based fingerprint acquisition pad 60 to positively identify the test subject. The collection chamber 40 is in fluid communication, generally, with the membrane test strips 51 and the immunoassay-based fingerprint acquisition pad 60. For example, a piping system, including plastic tubing and other structures, may fluidically couple these components.

The fluid collector 20 receives a fluid sample from a test subject and temporarily stores the fluid sample until it is transferred to the housing 30. In the preferred embodiment, the fluid sample is saliva, while in other embodiments, the fluid sample may be urine, blood, etc. Generally, any material capable of acquiring and storing a fluid sample may be used. In the preferred embodiment, a sponge 25 is attached to one end of the fluid collector 20 to absorb, and temporarily store, the fluid sample. The sponge 25 may be saturated with a saliva-producing substance such as, for example, citric acid, sodium chloride, etc. After the fluid sample has been collected, the fluid collector 20 is inserted into the collection chamber 40 through the opening 32, and the fluid sample is extracted therefrom by compressing the sponge 25 against the bottom surface of the lower portion 42 of the collection chamber 40, thereby releasing the entrapped fluid into the piping system.

Figure 4:
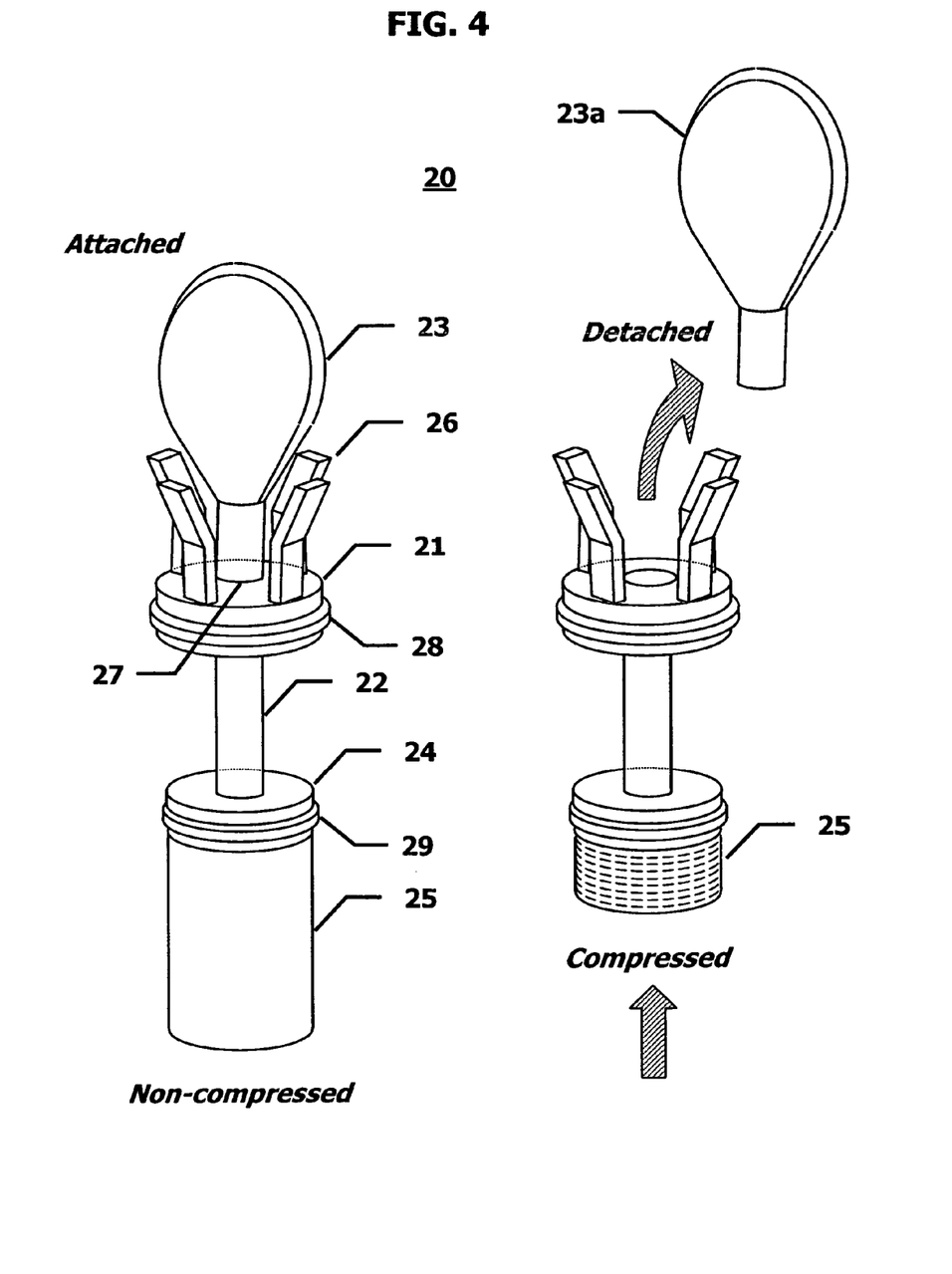
FIG. 4 depicts a two perspective views of a fluid collector in accordance with an embodiment of the present invention.
Figure 5:
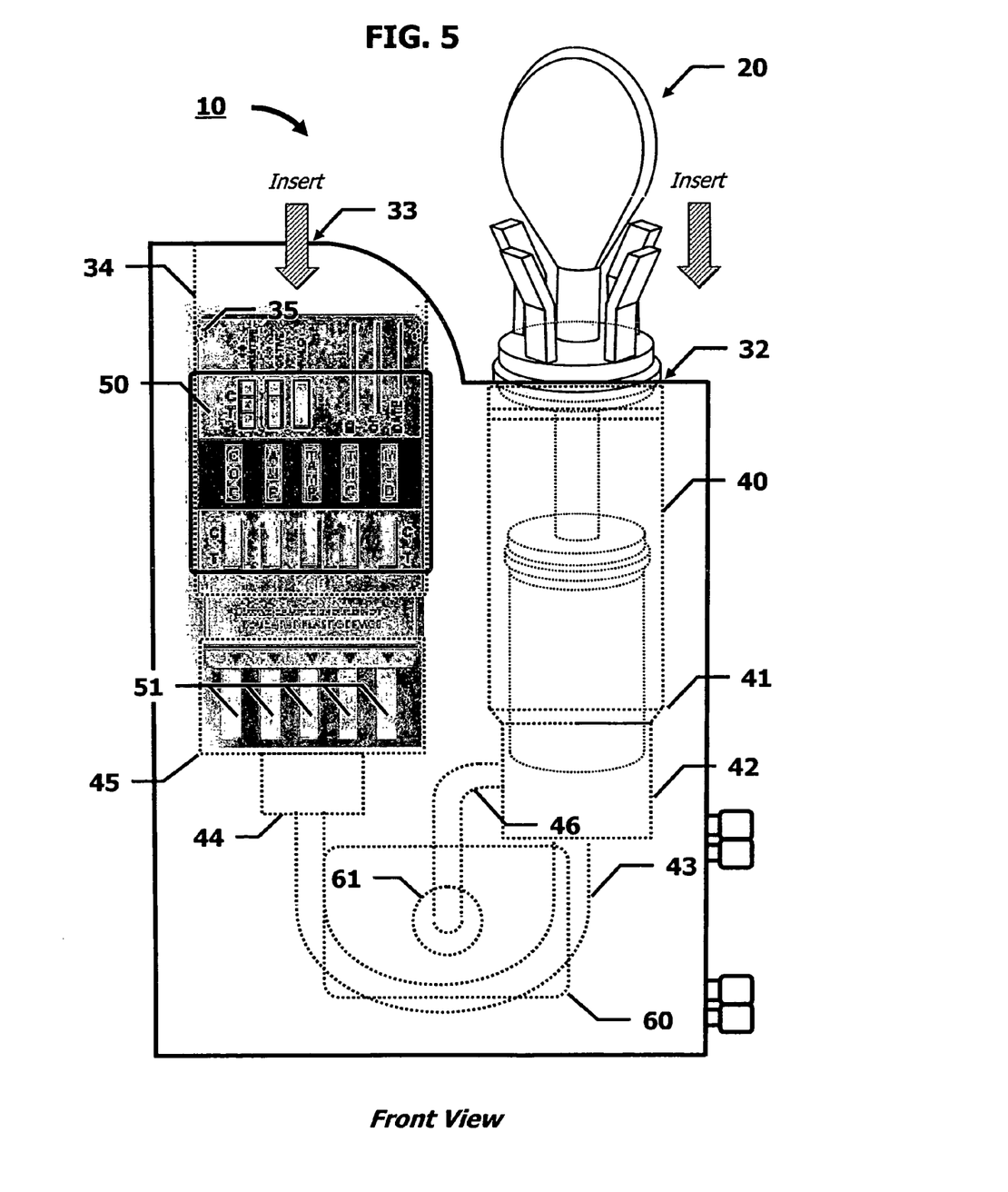
FIG. 5 depicts a front view of a fluid collection and drug testing device in accordance with an embodiment of the present invention.

The fluid collector 20 includes a central shaft 22, a disk 21, disposed at the upper end of the central shaft 22, a disk 24, disposed at the lower end of central shaft 22, and a handle 23 attached to the upper surface of the disk 21. In the depicted embodiment, the diameter of disk 21 is slightly larger than the diameter of disk 24. Additionally, sealing rings 28 and 29 may be attached to the outer circumference of disks 21 and 24, respectively. Generally, the dimensions of disks 21 and 24, and sealing rings 28 and 29, comport with the interior dimension of collection chamber 40 in order to prevent fluid from escaping through the opening 32. Sponge 25 is attached to the lower surface of disk 24 and is dimensioned to be slightly smaller in diameter than disk 24 to allow for radial expansion within the lower portion 42 of the collection chamber 40 when the sponge 25 is under compression.

Figure 1:
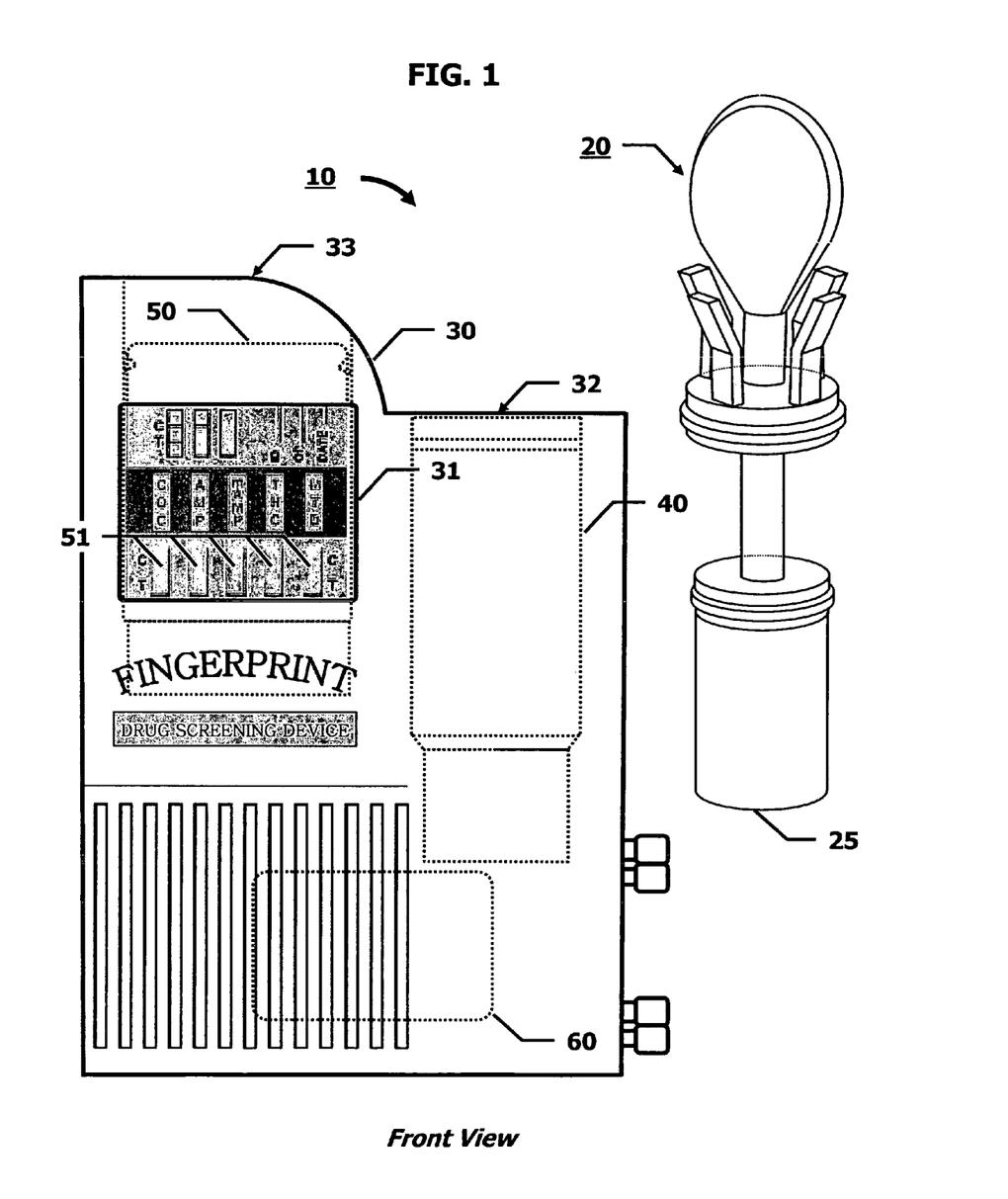
FIG. 1 depicts a front view of a fluid collection and drug testing device in accordance with an embodiment of the present invention.
Figure 2:
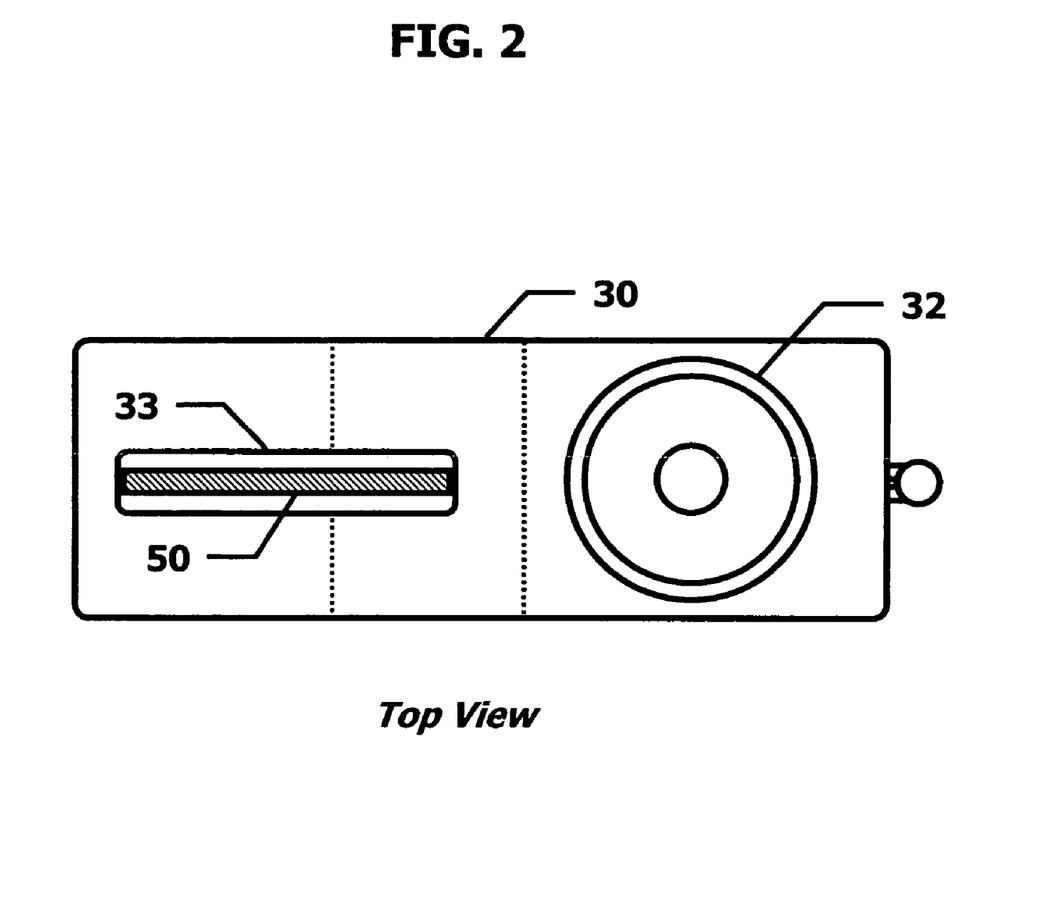
FIG. 2 depicts a top view of a fluid collection and drug testing device in accordance with an embodiment of the present invention.
Figure 3:
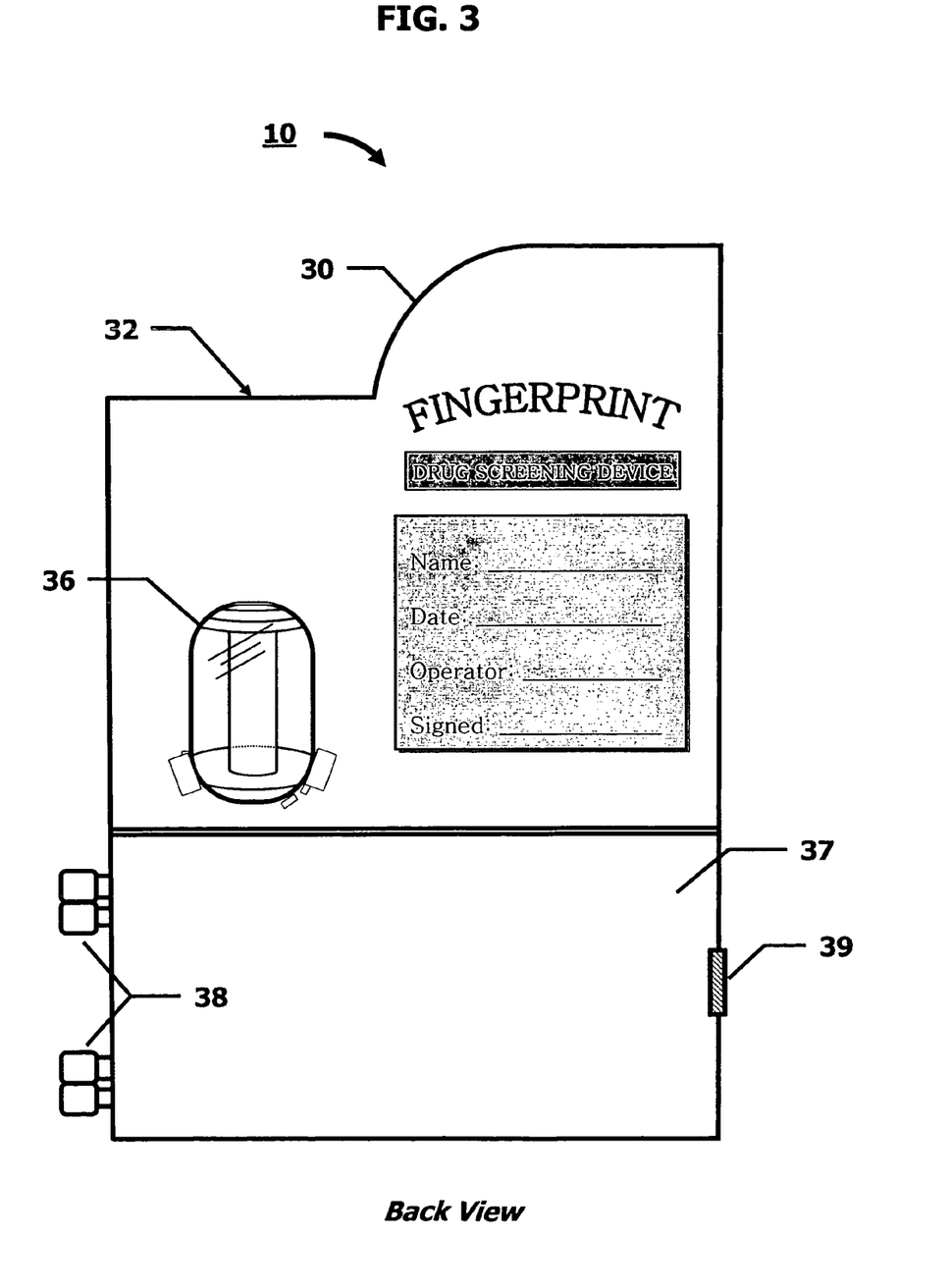
FIG. 3 depicts a back view of a fluid collection and drug testing device in accordance with an embodiment of the present invention.

As discussed in more detail below, the fluid collector 20 becomes secured within the collection chamber 40 after the fluid collector 20 is inserted into the collection chamber 40 to a predetermined depth. If desired, handle 23a may then be broken away from the upper surface of disk 21. The fingerprint drug screening device 10 also includes a window 36 through which the secured fluid collector 20 may be viewed. The cover 37 encloses immunoassay-based fingerprint acquisition pad 60, and is attached to the housing 30 by the hinges 38. The cover 37 may be secured after the fingerprint of the test subject has been acquired, using various locking mechanisms, such as a tab-and-slot arrangement, security tape, etc. Further confirmation testing may be performed, such as gas chromatography/mass spectrometry, gas chromatography/tandem mass spectrometry, etc., using the secured fluid sample. Access to the fluid sample may be obtained, for example, by simply removing the immunoassay-based fingerprint acquisition pad 60 to expose adapter 61 and tube 46, by puncturing the immunoassay-based fingerprint acquisition pad 60 with a needle to access adapter 61 and tube 46, etc.

The test cartridge 50, containing the membrane test strips 51, may be inserted into a test cartridge chamber 34 through an opening 33. Advantageously, different versions of the test cartridge 50 may be developed to test different combinations of drugs, thereby allowing the test administrator to select the appropriate drug test suite at the test site. The test cartridge chamber 34 may include a locking mechanism 35 to secure the test cartridge 50 within the test cartridge chamber 34, thereby preventing the removal of the test cartridge 50 from housing 30. The locking mechanism 35 cooperates with corresponding structure located on the test cartridge 50, and may include, for example, opposing teeth, a locking tab-and-slot arrangement, etc. Alternatively, the test cartridge 50 may be manufactured as an integral component of the device, in which case the opening 33 in the housing 30, and the locking mechanism 35, are not required. An opening or window 31 in the housing 30 allows a portion of the test cartridge 50 to be viewed, including, of course, the test and control regions of the membrane test strips 51.

Generally, each membrane test strip 51 indicates the presence or absence of one or more drugs. In the depicted embodiment, a single drug, or class of drugs, is indicated by each membrane test strip 51, such as, for example, cocaine (COC), amphetamine (AMP), methamphetamine (mAMP), marijuana (THC), methadone (MTD), phencyclidine (PCP), morphine, barbiturates, benzodiazepines, alcohol, etc. The minimum concentration level at which the presence of any particular drug is detected may be determined by various industry minimum standards, such as, for example, the National Institute on Drug Abuse (NIDA), the Substance Abuse & Mental Health Services Administration (SAMHSA), the World Health Organization (WHO), etc.

Immunoassay-based fingerprint acquisition pad 60 includes a compressible, porous reaction medium, having a control zone and a plurality of reaction zones, arranged on a porous support. The control zone includes a control reagent to identify the fluid sample donor, while each reaction zone includes a reaction reagent to determine the presence of a specific test substance (e.g., drug) in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

In one embodiment, immunoassay-based fingerprint acquisition pad 60 is fluidicly coupled to the collection chamber 40. A signal-producing agent, located on upper surface of the porous support or the lower surface of the reaction medium, mixes with the fluid sample provided to the immunoassay-based fingerprint acquisition pad 60. The production of an image or pattern which identifies the person providing the sample is accomplished by applying a fingertip to the upper surface of the reaction medium and compressing the reaction medium so that the fluid sample/signal-producing agent mixture permeates the reaction medium, and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Generally, a piping system fluidicly couples the collection chamber 40 to the membrane test strips 51 and the immunoassay-based fingerprint acquisition pad 60. In the depicted embodiment, tube 43 fluidicly couples the lower portion 42 of the collection chamber 40 to adapter 44 and test cartridge fluid reservoir 45. Similarly, tube 46 fluidicly couples the lower portion 42 of collection chamber 40 to adapter 61, located just beneath immunoassay-based fingerprint acquisition pad 60. While tubes 43 and 46 are shown to be individually connected to the lower portion 42 of collection chamber 40, other configurations are also possible. For example, tube 43 may be the only connection to the lower portion 42 of collection chamber 40. In this example, a "T" connection may be incorporated into tube 43 to fluidicly couple tube 46 to immunoassay-based fingerprint acquisition pad 60. Alternatively, the required fluid connections may be molded directly within the housing 30.

Figure 6:
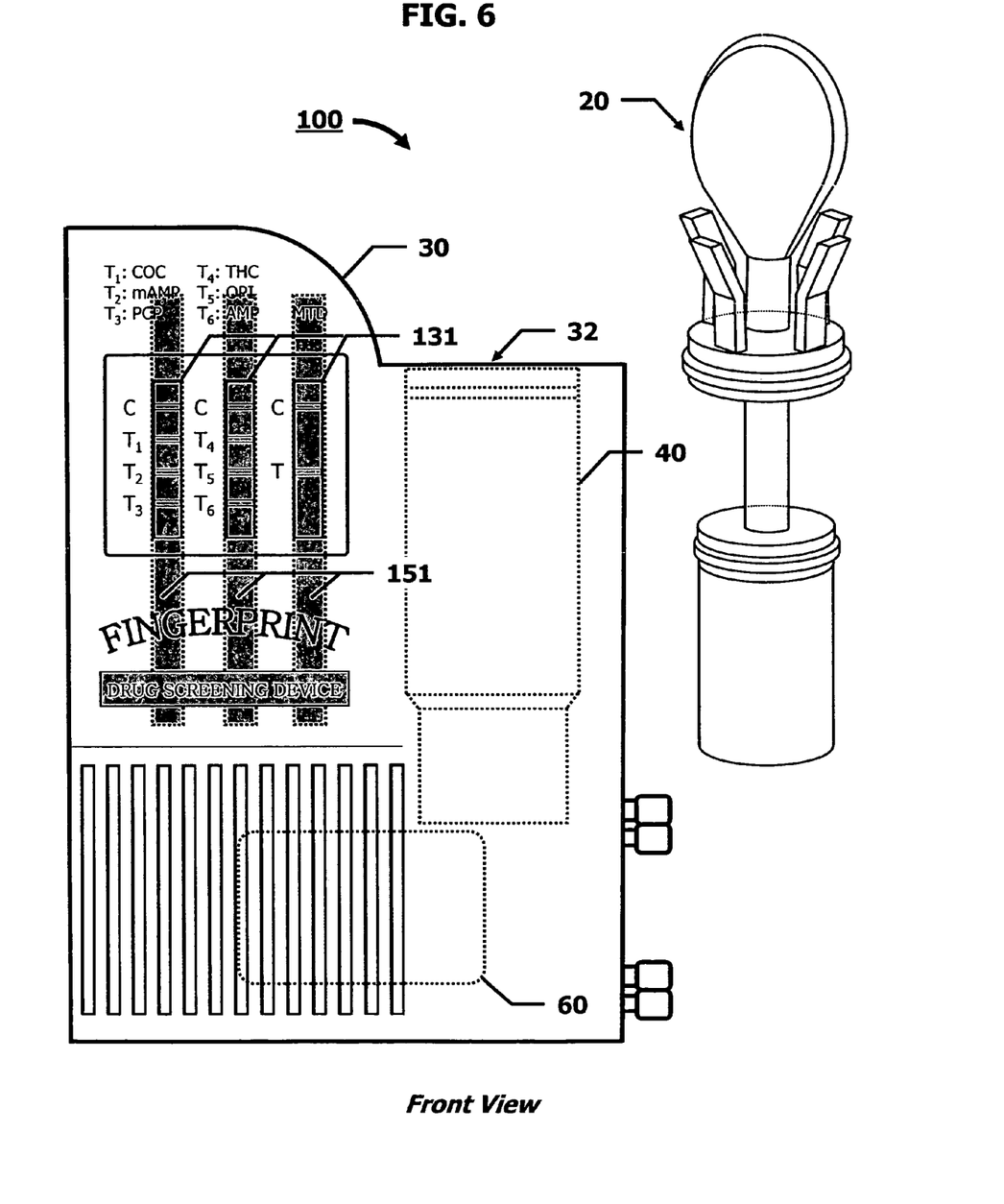
FIG. 6 depicts a front view of a fluid collection and drug testing device in accordance with an embodiment of the present invention.
Figure 7:
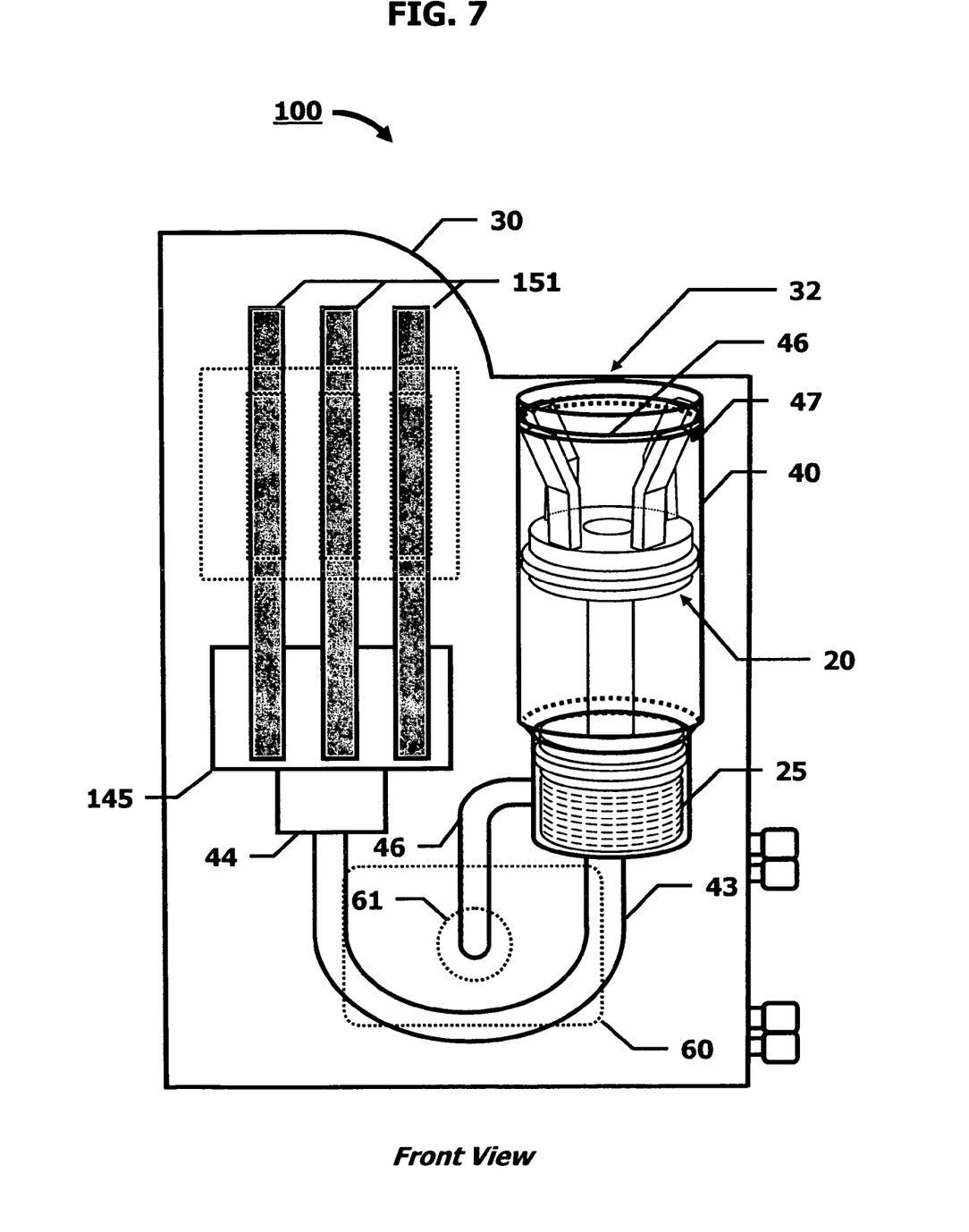
FIG. 7 depicts a front cutaway view of a fluid collection and drug testing device in accordance with an embodiment of the present invention.
Figure 8:
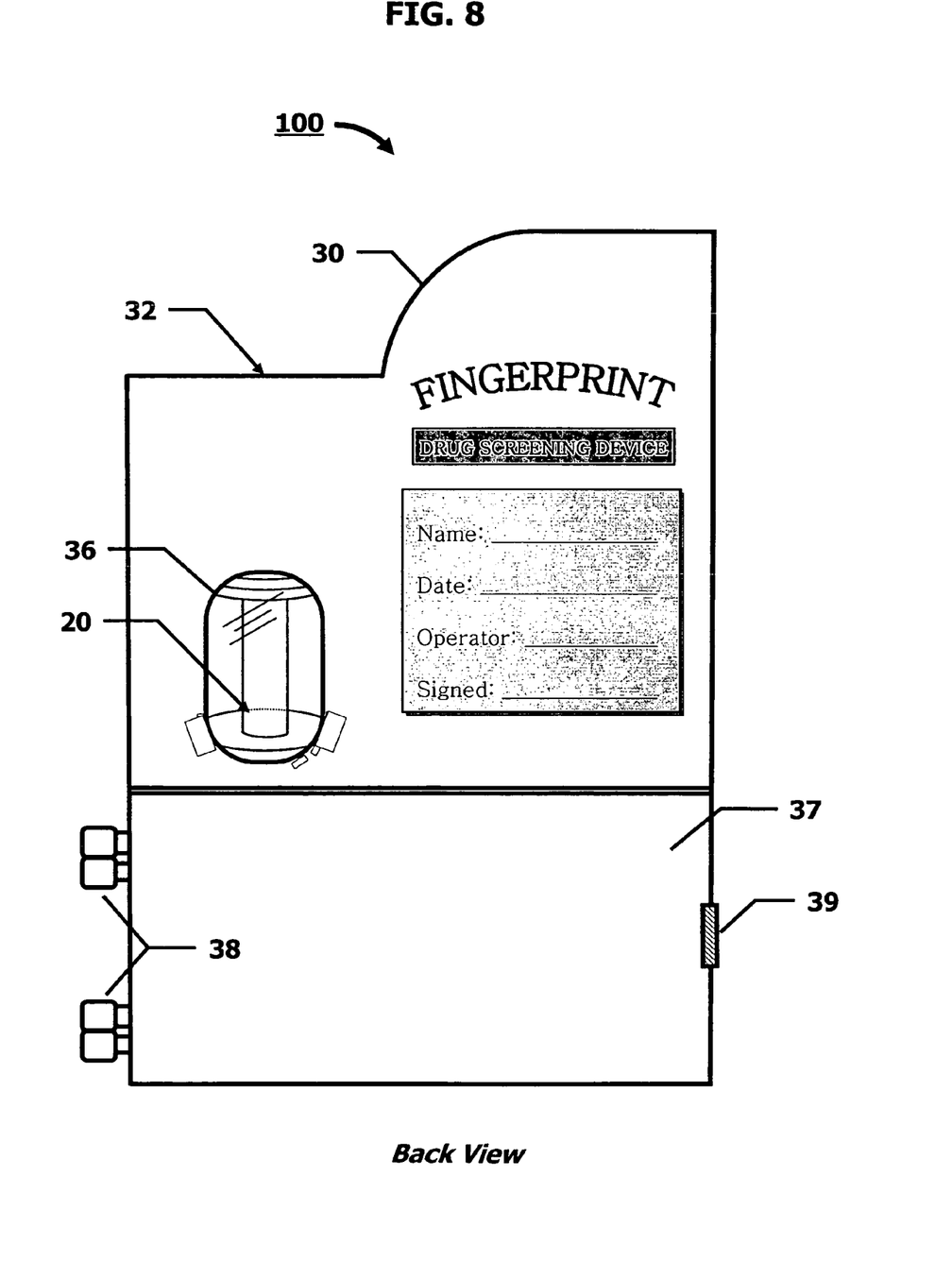
FIG. 8 depicts a back view of a fluid collection and drug testing device in accordance with an embodiment of the present invention.

FIGS. 6-8 depict a fluid collection and drug testing device in accordance with another embodiment of the present invention, which also employs the embodiment of the fluid collector 20 depicted in FIG. 4. In this embodiment, fingerprint drug screening device 100 includes membrane test strips 151 attached directly to housing 30. The membrane test strips are coupled to a fluid reservoir 145. In the depicted embodiment, several drugs are indicated by each membrane test strip 151, such as, for example, cocaine (COC), methamphetamine (mAMP) and phencyclidine (PCP) (leftmost strip), marijuana (THC), opiates and amphetamine (AMP) (middle strip) and methadone (MTD) (rightmost strip). In additional to recognized standards, minimum concentration levels at which a positive reaction is produced, i.e., no visible line in the test region of the membrane test strip, may include, for example, amphetamine (50 ng/mL), methamphetamine (50 g/mL), a cocaine metabolite including benzoylecgnonine and ecgonine methyl ester (20 ng/mL), an opiate including morphine, codeine and heroine (40 ng/mL), marijuana (THC COOH) (12 ng/mL) and phencyclidine (10 ng/mL). Several openings or windows 131 in the housing 30 allow the test and control regions of the membrane test strips 151 to be viewed.

As described above, the fluid collector 20 receives a fluid sample from a test subject and temporarily stores the fluid sample until it is transferred to the housing 30. The fluid collector 20 is then inserted into the collection chamber 40 through the opening 32, and the fluid sample is extracted therefrom by compressing the sponge 25 against the bottom surface of the lower portion 42 of the collection chamber 40, thereby releasing the entrapped fluid into the tubes 43 and 46. In an embodiment, projections 26 extend from the upper surface of disk 21 and cooperate with an annular projection 46, located on the inner surface of the collection chamber 40, to secure the fluid collector 20 within the collection chamber 40.

As depicted in FIGS. 7 and 8, after the fluid collector 20 is inserted a predetermined distance, the projections 26 engage the annular projection 46 to prevent the fluid collector 20 from being extracted from the collection chamber 40. While four projections are depicted, at least two should be used to effectively secure the fluid collector 20 within the collection chamber 40. Alternatively, the annular projection 46 may cooperate with a projecting circumferential ring (not show), located above the sealing ring 28 of disk 21, to secure the fluid collector 20 within the collection chamber 40. As an additional measure of security, handle 23a may be detached from the fluid collector 20 along a line of weakness 27 after the fluid collector 20 has engaged the annular projection 46. If a twisting motion is desired to detach the handle 23a from the fluid collector 20, then one (or more) stop(s) 47 may be located just below the annular projection 46 to prevent the fluid collector 20 from rotating by engaging one (or more) of the projections 26.

Figure 9:
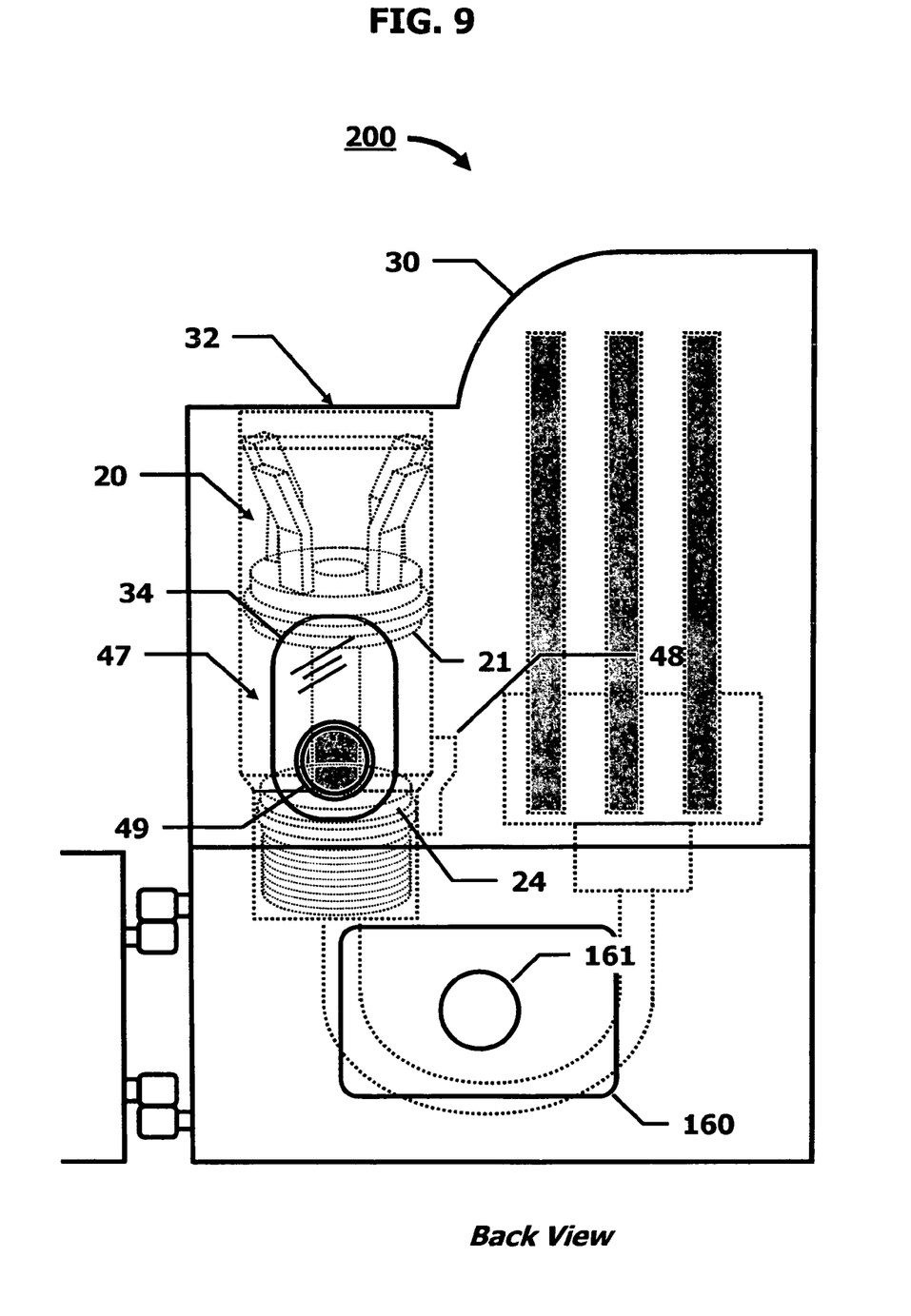
FIG. 9 depicts a back view of a fluid collection and drug testing device in accordance with an embodiment of the present invention.

FIG. 9 depicts a fluid collection and drug testing device in accordance with further embodiments of the present invention. In one embodiment, fingerprint drug screening device 200 includes a window 37 incorporating a sealable opening 49 that allows access to the collection chamber 40. When the fluid collector 20 is secured within the collection chamber 40, sealable opening 49 allows access to a confirmation chamber 47 formed between the disks 21 and 24. In another embodiment, a passage 48 fluidicly couples the lower portion 42 of the collection chamber 40 to the confirmation chamber 47 to allow a portion of the fluid sample to flow into the confirmation chamber 47 as the fluid collector 20 is inserted into the collection chamber 40. Once the fluid collector 20 is secured with the collection chamber 40, a portion of the fluid sample is available for confirmation sampling through the sealable opening 49.

In one embodiment, immunoassay-based fingerprint acquisition pad 60 is not fluidicly coupled to the collection chamber 40. Instead, a portion of the fluid sample is extracted through the sealable opening 49, using, for example, a pipette, and applied to the upper surface of immunoassay-based fingerprint acquisition pad 60. A signal-producing agent is applied to the person's fingertip, or, alternatively, the signal-producing agent may be located on the upper surface of the porous support or the lower surface of the reaction medium. The signal-producing agent then mixes with the fluid sample provided to the immunoassay-based fingerprint acquisition pad 60. The production of an image or pattern which identifies the person providing the sample is accomplished by applying a fingertip to the upper surface of the reaction medium and compressing the reaction medium so that the fluid sample permeates the reaction medium, and allowing the predetermined ligand/receptor reaction to take place so that the members of the immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

In other embodiments, immunoassay-based fingerprint acquisition pad 160 may be replace with an inkless fingerprint pad, or the like, to simply identify the test subject without testing for specific substances.

While this invention has been described in conjunction with specific embodiments thereof, many alternatives, modifications and variations will be apparent to those skilled in the art. Accordingly, the preferred embodiments of the invention as set forth herein, are intended to be illustrative, not limiting.

Various changes may be made without departing from the true spirit and full scope of the invention as set forth herein.

What is claimed is:

1. A fluid collection and drug testing device, comprising:
   a fluid collector to collect a fluid sample; and
   a housing, to test and retain the fluid sample, including:
      a collection chamber, having an open end, to receive the fluid collector,
      at least one membrane test strip, in fluid communication with the collection chamber, to indicate the presence or absence of at least one test drug, and
      an immunoassay-based fingerprint acquisition pad in fluid communication with the collection chamber.

2. The device of claim 1, wherein the housing includes a test cartridge chamber, having a portion in fluid communication with the collection chamber, to receive and secure a test cartridge within the device, the test cartridge containing said at least one membrane test strip.

3. The device of claim 1, wherein the fluid collector includes:
   a first disk, located at a distal end of a central shaft, having a first circumferential seal;
   a handle attached to an upper surface of the first disk;
   a second disk, located at a proximal end of the central shaft, having a second circumferential seal; and
   a sponge, attached to a lower surface of the second disk, to absorb the fluid sample.

4. The device of claim 3, wherein an inner surface of the collection chamber includes an upper annular projection, proximate to the open end, to secure the fluid collector within the collection chamber after the fluid collector has been inserted into the collection chamber.

5. The device of claim 4, wherein the fluid collector includes a plurality of projections, attached to the upper surface of the first disk, to cooperate with the annular projection and secure the fluid collector within the collection chamber after the fluid collector has been inserted into the collection chamber.

6. The device of claim 4, wherein the handle is removably attached to the upper surface of the first disk.

7. The device of claim 1, wherein the immunoassay-based fingerprint acquisition pad includes:
   at least one control zone including a control reagent to identify the fluid sample donor, the reagent including a member of a predetermined ligand/receptor binding pair; and
   a plurality of reaction zones, each of which includes a reaction reagent to determine the presence of a specific test drug in the fluid sample, the reaction reagent including a member of a predetermined ligand/receptor binding pair.

8. The device of claim 7, wherein the immunoassay-based fingerprint acquisition pad is enclosed by a lockable cover attached to the housing.

9. The device of claim 1, wherein the fluid collector sponge is saturated with a saliva producing substance.

10. The device of claim 9, wherein the saliva producing substance includes citric acid and sodium chloride.

11. The device of claim 1, wherein said at least one membrane test strip includes:
   a dye region, disposed at a proximal end of the membrane test strip, including colloidal gold particles coated with mouse monoclonal antibodies specific to each of said at least one test drug;
   a control region, disposed at a distal end of the membrane strip, including goat polyclonal antibodies against gold-protein conjugate; and
   a test region, disposed between the dye region and the control region, including a drug-protein conjugate specific to each of said at least one test drug.

12. The device of claim 11, wherein the control region displays a visual indicator when the first volume of fluid received from the fluid collector is above a predetermined threshold and proper membrane wicking has occurred.

13. The device of claim 12, wherein the predetermined threshold is 200 microliters.

14. The device of claim 11, wherein the test region displays a visual indicator when the concentration of the membrane test drug in the fluid sample is below a predetermined threshold.

15. The device of claim 1, wherein said at least one membrane test strip identifies the presence or absence of a specific test drug within the fluid sample, including amphetamine, methamphetamine, a cocaine metabolite, an opiate, THC-COOH and phencyclidine.

16. The device of claim 15, wherein the absence of the specific test drug is indicated by the presence of a visual indicator on the membrane strip.

17. The device of claim 15, wherein the presence of a test drug is indicated by the absence of a visual indicator on the membrane strip.

18. A fluid collection and testing device, comprising:
   a fluid collector, to collect a fluid sample, including:
      a first disk, located at a distal end of a central shaft, having a first circumferential seal,
      a handle attached to an upper surface of the first disk,
      a second disk, located at a proximal end of the central shaft, having a second circumferential seal, and
      a sponge, attached to a lower surface of the second disk, to absorb the fluid sample; and
   a housing, including:
      a collection chamber, having an open end, to receive the fluid collector,
      at least one membrane test strip in fluid communication with the collection chamber, and
      an immunoassay-based fingerprint acquisition pad.

19. The device of claim 18, further comprising a fluid passage coupling a lower portion of the collection chamber to a middle portion of the collection chamber.

20. The device of claim 19, wherein the region between the first disk and the second disk forms a confirmation chamber within the middle portion of the collection chamber when the fluid collector is secured within the collection chamber.

21. The device of claim 20, further comprising a sealable opening, disposed in an outer wall of the housing, coupled to the confirmation chamber.

22. A fluid collection and testing device, comprising:
   a fluid collector, to collect a fluid sample, comprising a first disk, located at a distal end of a central shaft, having a first circumferential seal, a handle attached to an upper surface of the first disk, a second disk, located at a proximal end of the central shaft, having a second circumferential seal, and a sponge, attached to a lower surface of the second disk, to absorb the fluid sample; and
   a housing, including:
      a collection chamber, having an open end, to receive the fluid collector,
      at least one membrane test strip in fluid communication with the collection chamber, and
      an inkless fingerprint acquisition pad.

* * * * *